(12) United States Patent
Ma

(10) Patent No.: US 6,757,039 B2
(45) Date of Patent: Jun. 29, 2004

(54) PAPER WHITE CHOLESTERIC DISPLAYS EMPLOYING REFLECTIVE ELLIPTICAL POLARIZER

(76) Inventor: Yao-Dong Ma, 1866 Bethany Ave., San Jose, CA (US) 95132

(*) Notice: Subject to any disclaimer, the term of this patent is extended or adjusted under 35 U.S.C. 154(b) by 45 days.

(21) Appl. No.: 10/174,437

(22) Filed: Jun. 17, 2002

(65) Prior Publication Data

US 2003/0231266 A1 Dec. 18, 2003

(51) Int. Cl.[7] .......................... G02F 1/1335; G02F 1/13
(52) U.S. Cl. ........................... 349/115; 349/98; 349/175
(58) Field of Search ............................ 349/98, 115, 175

(56) References Cited

U.S. PATENT DOCUMENTS 6,067,136 A * 5/2000 Yamaguchi et al. .......... 349/96
6,414,910 B1 * 7/2002 Kaneko et al. ............. 368/242
6,542,208 B1 * 4/2003 Akiyama ..................... 349/96

* cited by examiner

Primary Examiner—Huyen Ngo

(57) ABSTRACT

This invention relates to paper white cholesteric displays employing a reflective elliptical polarizer. In the reflective mode, the paper white ON state is achieved by a reflective elliptical polarizer in display's planar texture area; and the black OFF state is obtained by cholesteric's depolarization effect and polarizer's filtration effect in display's focal conic texture area. In the transmissive mode, on the other hand, the paper white ON state is created by a back lighting projected onto the focal conic texture area; and the black OFF state is realized in the cholesteric planar texture area. The reflective elliptical polarizer with a broadband reflection and high polarization efficiency delivers a bright neutral white color to both the reflective and transmissive mode cholesteric displays. The reflective elliptical polarizer also provides a solution to the transflective display where the high efficiency front-lit mode and the back-lit mode can be converted automatically.

8 Claims, 6 Drawing Sheets

PAPER WHITE CHOLESTERIC DISPLAYS EMPLOYING REFLECTIVE ELLIPTICAL POLARIZER

BACKGROUND OF THE INVENTION

Cholesteric liquid crystal displays are characterized by the fact that the pictures stay on the display even if the driving voltage is disconnected. The bistability and multistability also ensure a completely flicker-free static display and have the possibility of infinite multiplexing to create giant displays and/or ultra-high resolution displays. In cholesteric liquid crystals, the molecules are oriented in helices with a periodicity characteristic of material. In the planar state, the axis of this helix is perpendicular to the display plane. Light with a wavelength matching the pitch of the helix is reflected and the display appears bright. If an AC-voltage is applied, the structure of the liquid crystals changes from planar to focal conic texture. The focal conic state is predominately characterized by its highly diffused light scattering appearance caused by a distribution of small, birefringence domains, at the boundary between those domains the refractive index is abruptly changed. This texture has no single optic axis. The focal conic texture is typically milky-white (i.e., white light scattering). Both planar texture and focal conic texture can coexist in the same panel or entity. This is a very important property for display applications, whereby the gray scale can be realized.

Current cholesterics displays are utilizing "Bragg reflection", one of the intrinsic properties of cholesterics. In Bragg reflection, only a portion of the incident light with the same handedness of circular polarization and also within the specific wave band can reflect back to the viewer, which generates a monochrome display. The remaining spectrum of the incoming light, however, including the 50% opposite handedness circular polarized and out-off Bragg reflection wave band, will pass through the display and be absorbed by the black coating material on the back surface of the display to ensure the contrast ratio. The overall light utilization efficiency is rather low and it is not qualified in some applications, such as a billboard at normal ambient lighting condition. The Bragg type reflection gives an impression that monochrome display is one of the distinctive properties of the ChLCD.

In many applications, human eyes are friendlier with full color spectrum, i.e., white color information written on the dark background. With the development of the flat panel display, more and more displays with neutral color have come into being, such as black-and-white STN display and AMTFT display, etc. Unfortunately, both of these approaches involve major disadvantages and limitations. The AMTFT displays are not true zero field image storage systems because they require constant power input for image refreshing. The STN displays do not possess inherent gray scale capability as a result of the extreme steepness of the electro-optical response curve of the display. To realize a gray scale, the resolution has to be reduced by using, for example, four pixels instead of one per area. Anywhere from one to four pixels are activated at a particular time to provide the gray scale effect. The AMTFT devices use semiconductors to provide memory effects and involve use of expensive, ultra high resistance liquid crystal materials to minimize RC losses. Additionally, these displays are both difficult and costly to produce and they are, at present, limited to relatively small size displays. The cholesteric display has many advantages over the STN and AMTFT display with its zero field memory effect, hemispheric viewing angle, gray scale capability and other optical performances, but it obviously needs to come up with black-and-white solution in order to keep its superiority.

U.S. Pat. No. 5,796,454 introduces a black-and-white back-lit ChLC display. It includes controllable ChLC structure, the first circular polarizer laminating to the first substrate of the cell which has the same circular polarity as the liquid crystals, the second circular polarizer laminating to the second substrate of the cell which has a circular polarity opposite to the liquid crystals, and a light source. The black-and-white back-lit display is preferably illuminated by a light source that produces natural "white" light. Thus, when the display is illuminated by incident light, the circular polarizer transmits the 50% component of the incident light that is right-circularly polarized. When the ChLC is in an ON state, the light reflected by the ChLC is that portion of the incident light having wavelengths within the intrinsic spectral bandwidth, and the same handedness; The light that is transmitted through the ChLC is the complement of the intrinsic color of ChLC. The transmitted light has right-circular polarization, however, it is thus blocked by left-circular polarizer. Therefore, the observer will perceive that region of the display to be substantially black. When the display is in an OFF state, the light transmitted through the polarizer is optically scattered by the ChLC. The portion of the incident light that is forward-scattered is emitted from the controllable ChLC structure as depolarized light. The left-circularly polarized portion of the forward-scattered light is transmitted through the left-circular polarizer, thus, is perceived by an observer. The black-and-white display, in '454 patent, is generated by back-lit component and the ambient light is nothing but noise.

U.S. Pat. No. 6,344,887 introduces a method of manufacturing a full spectrum reflective cholesteric display, herein is incorporated by reference. '887 teaches a cholesteric display employing absorptive polarizers with the same polarity but different disposition. The display utilizes an absorptive circular polarizer and a metal reflector film positioned on the backside of the display to guide the second component of the incoming light back to the viewer. However, the shortcoming of the Iodine type absorptive polarizer makes the display to take on a tint of color in the optical ON state, for example, greenish white. The reasons for that are described as follows: Firstly, all the absorptive iodine polarizer has a more or less blue leaking problem which causes non-neutral color of a display device. Secondly, the absorptive polarizer has limited transmission (44%) and polarization efficiency that causes the second reflection having less intensity than that of the first one. Thirdly, the metal reflector always has a limited reflectivity. Take the Aluminum for example, the reflectivity is in the range of 80~90%. Fourthly, the quarter waveform retardation film can only match a narrow wavelength of the light to generate a circularly polarized light. Addition to the multilayer surface mismatching, the total reflection of the back absorptive circular polarizer is around 35%. All those reasons result in a full spectrum cholesteric display appearing non-paper white.

SUMMARY OF THE INVENTION

It is the primary objective of the present invention to realize a paper-white reflection in display's planar texture while maintaining the cholesterics' superiority such as high contrast ratio, hemispheric viewing angle, zero-field long time memory and so on.

It is another objective of the present invention to create the dark state in display's focal conic texture so as to achieve a reflective type black-and-white display.

It is still another objective of the present invention to realize a paper-white transmission in focal conic texture when the display switches to back-lit working mode.

It is also another objective of the present invention to create the dark state in planar texture when the display switches to back-lit working mode so as to achieve a transmissive type black-and-white display.

It is another objective of the present invention to accomplish a theoretically best brightness of the front reflection.

It is still another objective of the present invention to utilize a broadband reflective elliptical polarizer as a key component to generate and guide the elliptical polarization.

It is a further objective of the present invention to take the advantage of the bipolarity characteristics of the cholesteric broadband elliptical polarizer to achieve a high efficiency front-lit and back-lit converting system.

It is also another objective of the present invention to obtain a brightness enhancement effect of the reflective elliptical polarizer.

DETAILED DESCRIPTION

Figure 1:
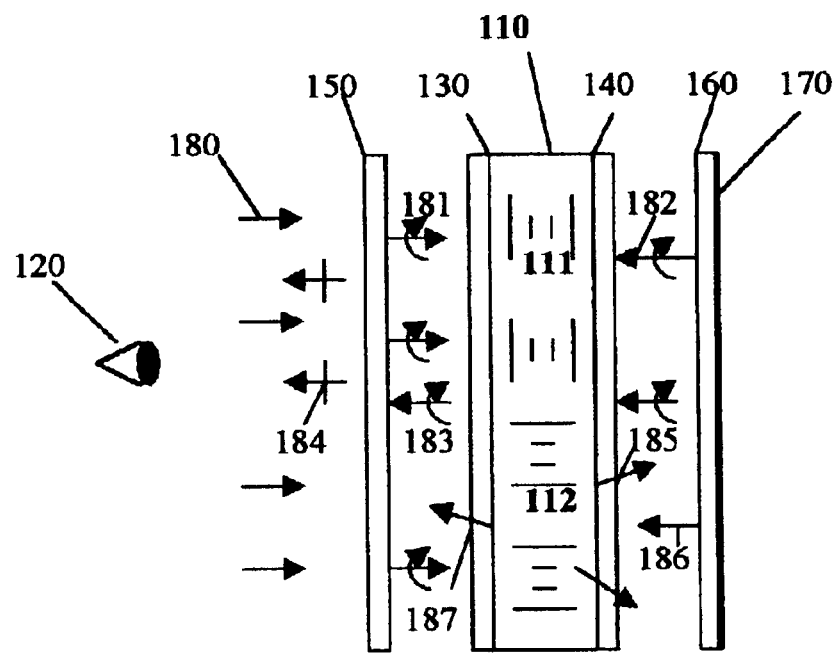
FIG. 1 shows a schematic display structure of a reflective elliptical polarizer, attached onto the back of a display cell, combined with a front absorptive elliptical polarizer.

Referring first to FIG. 1, illustrated is a front-lit black-and-white cholesteric display structure laminated with a front absorptive elliptical polarizer (AEP) and a back reflective elliptical polarizer (REP). The front AEP is made of an optimal retarder laminated with linear polarizer film in an optional angle. The back REP is made of a cholesteric polymeric film with an optical domain distribution other than a dichroic mirror surface. The natural light 180 first reaches the front AEP 150 with either the same handedness or opposite handedness to that of liquid crystal material 110, for example, the right-handed elliptical polarizer (RHEP) for the convenience of description. When the front AEP 150 has the same handedness as the LC material 110 and as the reflective elliptical polarizer (REP) 160, roughly 50% left-handed (LH) of incoming light is filtered by the AEP and approximately 50% right-handed (RH) 181 is allowed to pass through. The RH component then reaches the ChLC film 110 in planar texture area 111 and part of it will be reflected. The rest of it, which passes through the area 111 and hits on the REP 160, will be reflected (see light 182) by the REP made of a broadband cholesteric polymer film with the thickness in the range of 2~25 $\mu$m. Furthermore, the light 182 passes the planer area 111(see light 183), then the front AEP and finally emerges to the display front surface 184.

When the front AEP has the opposite handedness to the liquid crystal material 111 but the same handedness as the REP, the reflection from the planar texture will become almost zero, regardless whether the Bragg reflection is selected in the visible wavelength or in the invisible wavelength. The natural light first reaches the front AEP 150, for example, the right-handed elliptical polarizer (RHEP) for the convenience of description. Approximately 50% right-handed 181 is allowed to pass. Due to the opposite handedness with the left-handed LC material in the planar texture 111, all the RH light will pass through the ChLC cell structure without substantially attenuation. Only a small portion of the incident RH light with a large incident angle has a chance to reflect back (generally over 45°) and the majority of the RH light 182 will then be reflected back by the REP 160 made of broadband cholesteric polymer film. Furthermore, the light 182 passes the planer area 111(see light 183), then the front AEP and finally emerges to the display front surface 184. As a result, the bright white optical ON state will take on in the portion of the display's planar texture area.

As the ChLC display structure addressed in a focal conic texture 112, the display works in the optical OFF state. The incident light 180 reaches the front AEP 150 and is cut off more than 50%. The rest of it 181 gets to the ChLC cell with focal conic texture 112 and is depolarized by the scattering effect of the LC material. As the neutral non-polarized light 185 hits on the REP made of cholesteric broadband polymer, 50% right-handed polarized light will be reflected back 186 and the other 50% left-handed light, passing through the REP, will be absorbed by the black painting layer 170. The light 186 passes the ChLC cell again and becomes depolarized light 187 due to the focal conic scattering effect. The remaining non-polarized light reaches the first AEP and half of it is getting further lost. Finally, only a small portion of total light (less than 4%) will emerge to the front as scattered polarized light. The scattering emerged light has large viewing cone so that human eyes 120 perceive only a small portion of it. It is surprisingly discovered that the present invention has realized better blackness than that of the prior art.

The differences between U.S. Pat. No. 6,344,887 and the present invention in the optical ON state can be described as follows. In '887 patent two absorptive circular polarizers are designed in the same handedness, which not only have the same handedness with each other but keep the same handedness as the cholesteric liquid crystal material as well. The two circular polarizers are arranged in such a way that the retardation films contact with two sides of the display substrates respectively, while with one linear polarizer side toward the viewer and the other linear polarizer side toward the metal reflector. However, in the present invention, the reflective broadband cholesteric polarizer, which is attached to the back side of display's cell structure, has both the same handedness and opposite handedness relative to front AEP depending on the light incident direction. In the front-lit mode, the REP reflects the same handedness elliptical polarization generated by the front AEP.

In '887 patent, the Bragg reflection is not attenuated by the front circular polarizer because the same handedness as the liquid crystal material. In the present invention the Bragg reflection from the display's planar structure can be completely blocked by the front elliptical polarizer. The bright paper-white appearance attributes to the Bragg reflection from the reflective elliptical polarizer, made of a broadband cholesteric polymer film, which will substantially guide the light toward the viewer. REP has a very wide bandwidth and very high polarization efficiency when it works in the reflective mode.

The other fundamental difference of the present invention from the prior art is the simplicity of the display structure. The present invention doesn't utilize a metal reflector, nor a retardation film, nor a multi-layer absorptive linear polarizer at the back side of the display. In stead, the present invention utilizes a REP positioned at the back of the display substrate. For the first time in LCD history, the reflective cholesteric broadband polarizer has been properly used in the display as an independently functional component without combining a quarter wave retarder or a clean-up polarizer film as the prior arts did. Thus the principle of the present invention leads to the best application of the reflective polarizer wherein it posses much superior performances to that of the traditional absorptive polarizer.

What is the most important difference of those state of the art from the prior art is that the superior whiteness due to the high reflectivity and optimal angular distribution (average ellipticity of the REP). The present invention delivers a paper-white appearance with 45% reflectivity. The whiteness of the display is substantially determined by the angular distribution, i.e. the average ellipticity of the cholesteric REP film. A lot of experiments have been carried out to characterize the distribution of the REP. If the cholesteric polymer is characterized by a mirror reflection (reflective circular polarizer), a diffusing layer is necessary to enlarge its viewing angle. A diffuser film with a haze rate over 80% appears the best in whiteness compared with the lower one. The second approach is to produce the REP directly on a diffusive web surface during in-line coating process, which delivers a suitable surface profile or multi-domain structure that is similar to the real planar texture of a controllable ChLC display.

A variety of manufacturing processes has been reported to realize the broadband cholesteric circular polarizer from an intrinsic narrow band chiral material. It has been previously shown that by creating a pitch gradient in the cholesteric helix during a photo-polymerization process, the reflection could occur over the entire visible spectrum. Another manufacturing process is to introduce a pitch gradient in the helix during a two-step process in a cholesteric glass. First, the reflection bandwidth is adjusted by thermal annealing. Then the optical properties are permanently stored by quenching the viscous material to a glass at room temperature. The two steps, pitch gradient establishment and film hardening are independently controlled. The reflection may occur over a wavelength bandwidth greater than 300 nm. Still another manufacturing process is multi-layer in-line coating and curing process, each layer has a different helical pitch which will be polymerized sequentially. Broadband polarizers based on cholesteric liquid crystals have been disclosed in European Patent #94200026.6. The polarizers made use of the ChLC materials' selective reflection: reflection of circularly polarized light with the same handedness as the helical structure of the ChLC material, while transmitting the complementary component. The ChLC broadband polarizer shows much superior light efficiency compared to conventional absorptive polarizers. ChLC based broadband polarizers with high extinction ratios (>450 for reflection and >20 for transmission) in wide wavelength range (0.38~0.84 $\mu$m) have been reported. One may notice that the reflective mode ChLC polarizer has much higher extinction ratio than that of the transmissive mode. That means the circularly polarization generated from the reflection of the ChLC polarizer has very high purity which is higher than the absorptive circular polarizer made of one linear polarizer and one quarter wave retarder.

However, in the present invention, the traditional cholesteric circular polarizer with a mirror reflection cannot be directly used. To achieve a reflective cholesteric display with a large viewing angle, a cholesteric elliptical polarizer is preferred. The cholesteric domains in the polymeric structure have to be arranged in a certain angular distribution instead of the mirror surface as in the traditional broadband circular polarizer. The high extinction ratio of reflective elliptical polarization of the broadband ChLC polarizer perfectly meets the requirement of the cholesteric reflective display in terms of long term memory and bright front-lit display which consumes much less energy than that of the other displays. Obviously reflective type display mode is the primary and the most important application of the cholesteric display. The high polarization efficiency of the reflective elliptical polarizer results in a display with high brightness and paper whiteness.

Above all, with the whiter optical ON state and the darker optical OFF state, the present invention achieves a paper white display with a much better contrast ratio.

Figure 2:
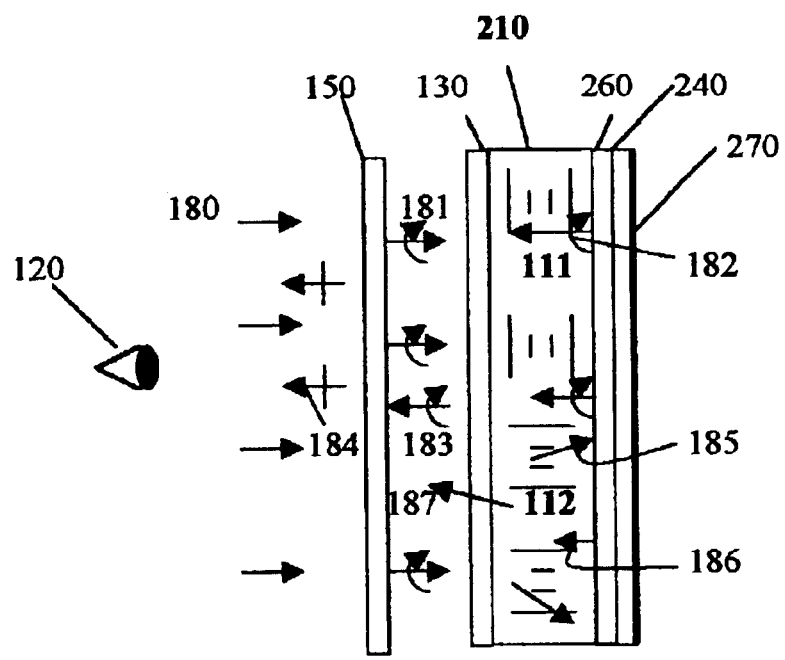
FIG. 2 shows a schematic display structure of a reflective elliptical polarizer, deposited inside of a display cell, combined with a front absorptive elliptical polarizer.

Turning now to FIG. 2, illustrated is a schematical display structure of a ChLC cell 210, an absorptive elliptical polarizer AEP 150, an internal cholesteric reflective elliptical polarizer REP 260 and a black coating layer 270. The structural simplicity of the REP allows it to be directly coated inside of the display cell structure as a part of the back substrate. The manufacture of the back substrate is described as follows. Firstly, the inside surface of the glass panel 240 is treated by an etching process to create a diffusive surface with haze rate over 60%. Secondly, on the diffusive surface, a multi-domain UV curable cholesteric pre-polymer material was coated with the thickness of 2~25 $\mu$m and then cured by UV beam in a suitable temperature condition. Thirdly, an over coating (OC) material is spin-coated on the top of the broadband cholesteric layer with the thickness of 1.7 $\mu$m and is thermo-cured completely. Fourthly, an ITO transparent conductive layer is sputtered on the top of the OC layer with the thickness of 0.18 $\mu$m. Finally, a chemical wet imaging process is carried out. A black coating layer or an equivalent back housing structure 270 is attached on the back of the substrate.

The working principle is almost the same as FIG. 1. The natural light 180 first reaches the front AEP 150 with either the same handedness or opposite handedness to that of liquid crystal material 110, for example, the right-handed elliptical polarizer (RHEP) for the convenience of description. When the front AEP 150 has the same handedness as the LC material 110 and as the reflective elliptical polarizer (REP) 160, roughly 50% left-handed (LH) of incoming light is filtered by the AEP and approximately 50% right-handed (RH) 181 is allowed to pass through. The RH component then reaches the ChLC film 110 in planar texture area 111 and part of it will be reflected. The rest of it, passing through the area 111 and hitting on the REP 260, will be reflected (see light 182) by the internal REP made of a broadband cholesteric polymer film. Furthermore, the light 182 passes the planer area 111(see light 183), then the front AEP and finally emerges to the display front surface 184.

When the front AEP has the same handedness as the REP but opposite handedness to the liquid crystal material 111, the reflection from the planar texture will become almost zero, regardless whether the Bragg reflection is selected in the visible or invisible wavelength. The natural light first reaches the front AEP 150, for example right-handed elliptical polarizer (RHEP) for the convenience of description. Approximately 50% right-handed 181 is allowed to pass. Due to the opposite handedness with the left-handed LC material in the planar texture 111, all the RH light will pass through the ChLC cell structure without substantially attenuation. Only a small portion of the incident RH light with a large incident angle has a chance to reflect back (generally over 45°) and majority of the RH light 182 will then be reflected back by the internal REP 260 made of broadband cholesteric polymer film. Furthermore, the light 182 passes the planer area 111(see light 183), then the front AEP and finally emerges to the display front surface 184. As a result, the bright white optical ON state will take on in the portion of the display's planar texture area.

As the ChLC display structure is addressed in a focal conic texture 112, the display works in optical OFF state. The incident light 180 reaches the front AEP 150 and more than 50% of the incident light is filtered out. The rest of it 181 gets to the ChLC cell with focal conic texture 112 and is depolarized by the LC material. The neutral non-polarized light 185 then hits on the internal REP 260 made of cholesteric broadband polymer and 50% right-handed polarized light will be reflected back 186. The other 50% left-handed light, passing through the REP, will be absorbed by the black painting layer 270. On the other hand, the light 186 passes back through the ChLC cell and becomes depolarized light 187 once more due to the focal conic scattering effect. The non-polarized remaining light reaches the first AEP and half of it is getting further lost. Finally, only a small portion of the total light (less than 4%) can reach the front as the scattered polarized light. The scattering emerged light has large viewing cone so that human eye 120 perceives only a small portion of it.

One of the advantages of internal structure of the REP is its completely parallax free when the polarizer has the opposite handedness to the controllable liquid crystal material. The other advantage of such structure is that the paper-white bright reflection because of the minimum optical loss.

Figure 3:
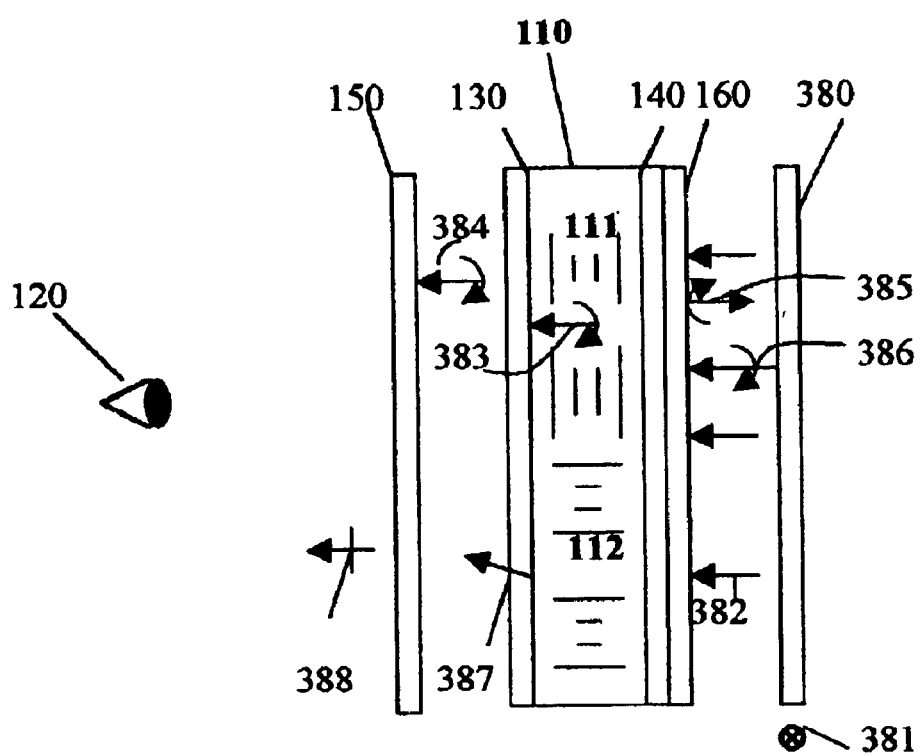
FIG. 3 shows a schematic back-lit display structure of a back lighting panel, a reflective elliptical polarizer, a display cell and a front elliptical polarizer.

Turning now to FIG. 3, illustrated is a back-lit black-and-white display. A back lighting system is positioned at the back of the display opposite to the viewer side. The lighting can be a CCFL pipe 381, or a white EL panel. When natural white light 382 out of the lighting panel hits on the broadband cholesteric elliptical polarizer, part of it passing through becomes left-handed elliptical polarized (LHEP) light 383 and part of it being reflected back and becomes right-handed elliptical polarization (RHEP) 385. The RHEP 385 then converts to LHEP 386 after bouncing back from the lighting panel. Note the portion of LHEP 386 is a recycled light, which will join in 383 to form LHEP 384. The front AEP has the exactly opposite polarity, so that it will substantially cut off the LHEP 386. As a result, the display takes on an optical dark state in the planar area.

On the other hand, when light 383 and recycled light 386 are passing through the display in focal conic texture area, they will become depolarized light 387. Finally, light 387, passing through the front AEP, travels out of the display panel and becomes the linear polarized light 388. The display will take on a white optical ON state in the focal conic area.

It is extremely important to render the lighting condition to the display during the nighttime or in the dark ambient light. In the prior art, the metal reflector attached to the back circular polarizer is opaque intrinsically. To obtain a back-lit mode, either a semi-transmissive Aluminum deposition or a perforated structure is utilized. Unfortunately, both the treatments will sacrifice the front reflection and hinder the back-lit transmission. The front-lit and the back-lit are always trade-off parameters in the prior arts, high front reflection means low transmission to the back-lit. By utilizing reflective cholesteric elliptical polarizer, however, the above-mentioned problem will be radically eliminated. First, the cholesteric elliptical polarizer has 50% transmission for one polarity of the elliptical polarization and 50% reflection for the other polarity of the elliptical polarization. It will not only reflect 100% front elliptical polarization during the front-lit mode, but also transmit 100% back light through its recycling effect when the back lighting system is switched on. In the present invention, back-lit display mode is a reverse version of the front-lit mode. Such reverse-mode display provides a pure white optical ON state in the focal conic area and a black optical OFF state in the planar texture area due to the opposite polarity of the front AEP and the back cholesteric elliptical polarizer. The brightness of the optical ON state in the reverse mode is extraordinary high because of the light recycling effect of the cholesteric elliptical polarizer.

The light recycling effect of the cholesteric elliptical polarizer, in the present invention, differentiates not only the absorptive elliptical polarizer when it works in the transmissive display mode but also the light recycling principle in the other display modes. In a normal back light condition, all the left-handed light passes through the polarizer while the right-handed component reflects back from the polarizer to the back light panel, where the right-handed component change its phase to the left-handed, and finally pass through the polarizer. The efficiency of the back lighting is so high that the power consumption of such back-lit system can be qualified as a best candidate of the portable electronics component. On the other hand, since the cholesteric display is an elliptical polarization modulator, the efficiency of the conversion from normal light to the elliptical polarization is intrinsically high, which doesn't need to convert further to the linear polarization as in the prior arts. For example, in TN or STN applications, the circular polarization generated by the reflective polarizer has to convert into the linear polarization by an attachment of a quarter wave retarder and a clean up absorptive polarizer which, indeed, results in a complicated optical system and low light efficiency.

Figure 4A:
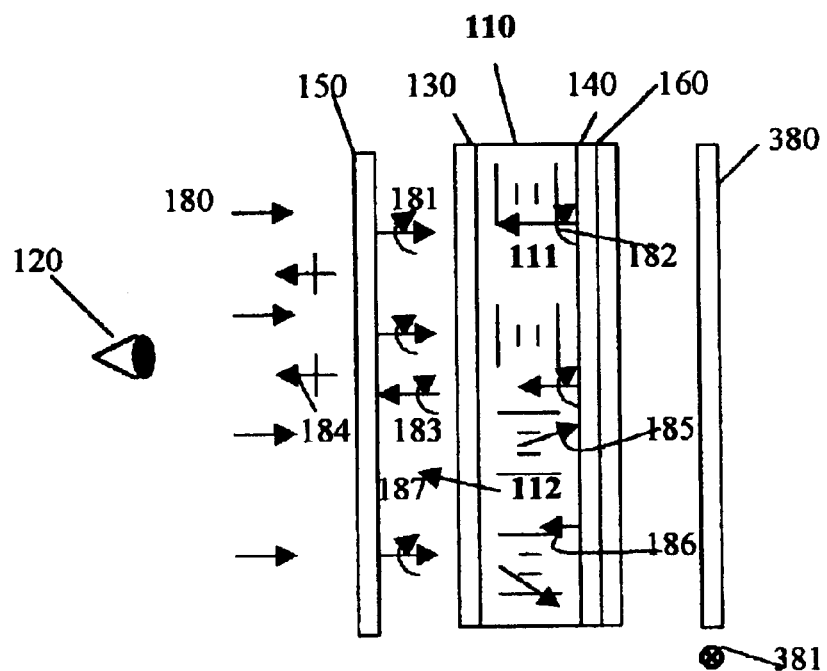
FIG. 4 shows schematic dual-mode display structures where 4A represents front-lit mode and 4B represents the back-lit mode.
Figure 4B:
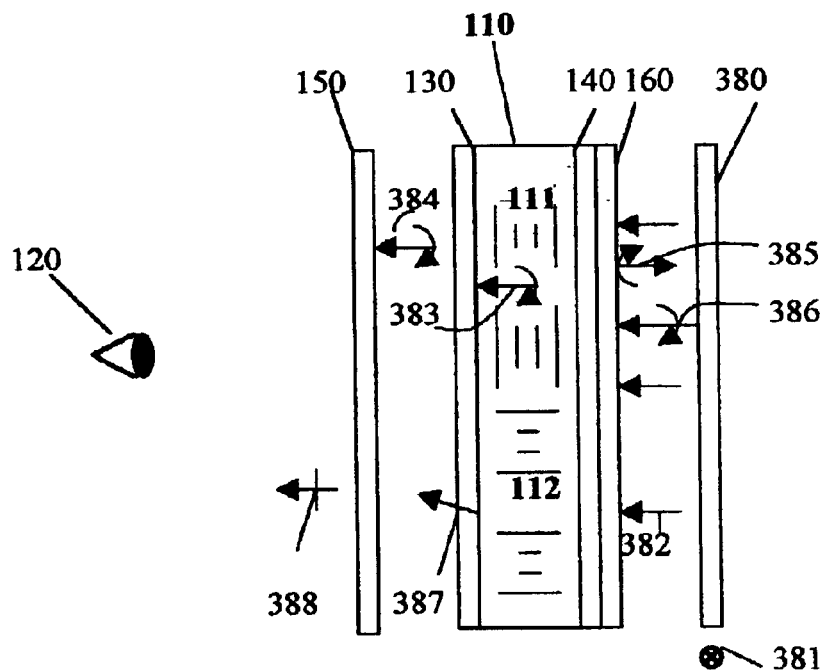

Turning now to FIG. 4A and FIG. 4B, illustrated is a dual-mode black-and-white ChLC display. The display will be able to work in both reflective and transmissive mode. Herein the broadband cholesteric polarizer serves as a key buffer component. Suppose that in reflective display mode, the light reflected from the broadband cholesteric polarizer is right-handed elliptical polarization. Then in the transmissive display mode, the light transmitted through the broadband cholesteric polarizer will be left-handed elliptical polarization. The bi-polarity of such wide band reflective polarizer delivers a most important performance. For the first time in LCD history, dual-working mode display with very high converting efficiency has come into being. During the daytime or in a strong ambient light condition, the display will work in the reflective mode, and both the front absorptive polarizer and the back reflective polarizer are arranged in the same polarity, i.e. the same handedness, so that the optical ON state will take on in the planar texture and the optical OFF state in the focal conic texture. On the other hand, during the nighttime or in a dark ambient light condition, the display works in the back lighting mode. The front absorptive polarizer and the back reflective polarizer are arranged in the opposite polarity, i.e. the opposite handedness, so that the optical ON state will take on in the focal conic texture and optical OFF state in the planar texture. FIG. 4A shows a schematic drawing of the dual-mode display working in the front-lit mode. The natural light 180 first reaches the front AEP 150 with either the same handedness or opposite handedness to that of liquid crystal material 110, for example, the right-handed elliptical polarizer (RHEP) for the convenience of description. When the front AEP 150 has the same handedness as the LC material 110 and as the reflective elliptical polarizer (REP) 160, roughly 50% left-handed (LH) of incoming light is filtered by the AEP and approximately 50% right-handed (RH) 181 is allowed to pass through. The RH component then reaches the ChLC film 110 in planar texture area 111 and part of it will be reflected. The rest of it, passing through the area 111 and hitting on the REP 160, will be reflected back 182 by the REP made of a broadband cholesteric polymer film. Furthermore, the light 182 passes through the planer area 111(see light 183), then through the front AEP and finally emerges to the display front surface 184.

When the front AEP has the opposite handedness to the liquid crystal material 111 but the same handedness as the REP, the reflection from the planar texture will become almost zero, regardless whether the Bragg reflection is selected in the visible or invisible wavelength. The natural light first reaches the front AEP 150, for example, the right-handed elliptical polarizer (RHEP) for the convenience of description. Approximately 50% right-handed 181 is allowed to pass. Due to the opposite handedness with the left-handed LC material in the planar texture 111, all the RH light will pass through the ChLC cell structure without substantially attenuation. Only a small portion of the incident RH light with a large incident angle has a chance to reflect back (generally over 45°) and the majority of the RH light 182 will then be reflected back by the REP 160 made of broadband cholesteric polymer film. Furthermore, the light 182 passes through the planer area 111(see light 183), then through the front AEP and finally emerges to the display front surface 184. As a result, the bright white optical ON state will take on in the portion of the display's planar texture area.

As the ChLC display structure is addressed in a focal conic texture 112, the display works at optical OFF state. The incident light 180 reaches the front AEP 150 and is cut off more than 50%. The rest of it 181 gets to the ChLC cell with focal conic texture 112 and is depolarized by the LC material. The sufficiently neutral non-polarized light 185 then hits on the REP made of cholesteric broadband polymer and 50% right-handed polarized light will reflect back 186. The other 50% left-handed light passing through the REP will be absorbed by the back housing between the display panel and the back lighting panel. Take an EL panel, for example, no matter what color the EL panel is (white EL takes pink color in power-off state), the black housing effect is truly good enough to create a satisfied black dark state in the focal conic area of the display. The light 186 passes the ChLC cell again and becomes depolarized light 187 due to the focal conic scattering effect. The remaining non-polarized light reaches the first AEP and half of it is being further lost. Finally, only a small portion of the total light (less than 4%) can escape to the front as scattered polarized light. The scattering emerged light has large viewing cone so that human eyes 120 perceive only a small portion of it. With the whiter optical ON state and the darker optical OFF state, the present invention achieves a paper white display with much better contrast ratio.

FIG. 4B shows the dual-mode display working in the back-lit mode, which is exactly the same as the FIG. 3. A back lighting system is positioned at the back of the display opposite to the viewer side. The lighting can be a CCFL pipe 381, or a white EL panel. When natural white light 382 out of the lighting panel passes through the broadband cholesteric elliptical polarizer, part of it becomes left-handed elliptical polarized (LHEP) light 383 and part of it being reflected back and becomes right-handed elliptical polarization (RHEP) 385. The RHEP 385 then converts to LHEP 386 after bouncing back from the lighting panel due to a 180-degree phase shift. Note, the portion of LHEP 386 is a recycled light, which will join in 383 to form LHEP 384. The front elliptical polarizer has the exactly opposite polarity, so that it will substantially cut off the LHEP 386. As a result, the display takes on an optical dark state in the planar area.

On the other hand, when light 383 and recycled light 386 are passing through the display in focal conic texture area, they will become depolarized light 387 because of a strong scattering between LC domains. Finally, light 387 passed through the front absorptive polarizer, reaches out of the display panel and becomes linear polarized light 388. The display will takes on an optical ON state in the focal conic area.

An electronic controller and a power supply system enable the conversion between the front-lit and the back-lit display to achieve the required version of image on the display. For example, if a reader requires a black character on the white background (paper-type), the information to be displayed should be switched to an inverse optical state simultaneously as the lighting mode changes in order to avoid the inverse image during the mode transformation.

The differences of the dual working mode from the U.S. Pat. No. '454 are that, firstly, '454 belongs to a monochrome (green/yellow) front lit mode and black-and-white back-lit mode display. Secondly, '454 utilizes a PDLC (Polymer dispersed liquid crystal) panel as a buffer component between the front-lit and back-lit mode, which is a rather cumbersome and power hungry solution. Thirdly, the absorptive back polarizer attenuate at least 50% back-lit energy without any light recycling performance which causes the back-lit mode very dim appearance. On the contrary, the present invention creates a dual working mode black-and-white display with high efficiency (high transmission plus recycle) and simpler structure (no retarder film, no PDLC shutter on the back of the display).

Still, the other difference of the dual working mode of the present invention from the prior art U.S. Pat. No. '887 is that the latter uses a semi-transmissive aluminum reflector as a buffer component. As mentioned above, the semi-transmissive reflector always creates a trade-of effect to the display in a way that high transmission of the back-lit results in low reflection to the front-lit mode and vice versa. Secondly, the latter cannot produce the black-and-white display in the back-lit mode. Still, there exists low light converting efficiency, which is the same problem as that in U.S. Pat. No. '454.

High light converting effect of the present invention allows the display to adopt a super thin but low illuminant EL panel as the back lighting system. This is very important in the portable electronics display devices.

Figure 5A:
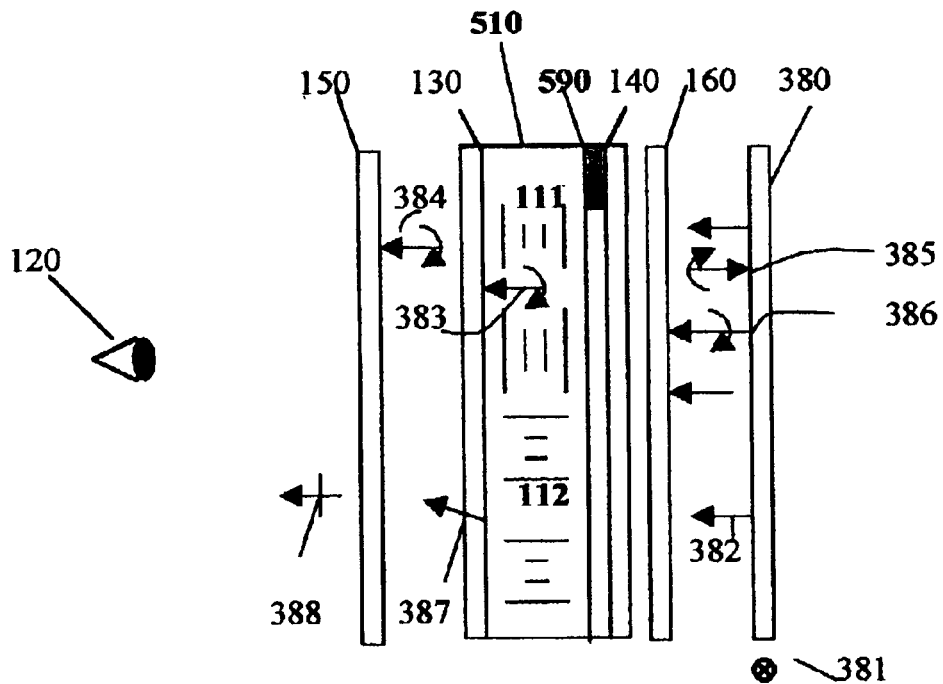
FIG. 5 shows a schematic full color display structure where 5A represents a dual-mode front and back-lit color display and 5B represents a front-lit black-and-white display and back-lit full color display.

Turning now to FIG. 5, illustrated is a dual working mode, full color cholesteric display. A color filter layer is fabricated inside the display's cell structure. FIG. 5A shows a sectional structure of dual-mode full color display where an absorptive color filter 590 is deposited on the back substrate 140. In the front-lit mode, front AEP 150 has the same polarity as the REP 160 but opposite to the cholesteric liquid crystals inside the display cell 110. The Bragg reflection out of 110 will be substantially cut off by the front AEP 150, so that the color information is merely generated by the REP 160 and the color filter 590. The color optical ON state takes on in the planar texture area, and the black optical OFF state in the focal conic texture area respectively.

In the back-lit mode, the front ACP 150 has the opposite polarity to the reflective polarizer. A back light emitting from light panel 380 passing REP 160 becomes the left polarized light without substantially attenuation. The light, which passing through the color filter 590 and through the ChLC layer 111 will be blocked by the 150. On the other hand, the color light that travels through the ChLC's focal conic texture 112 will be depolarized and finally emerges to the front viewer.

Figure 5B:
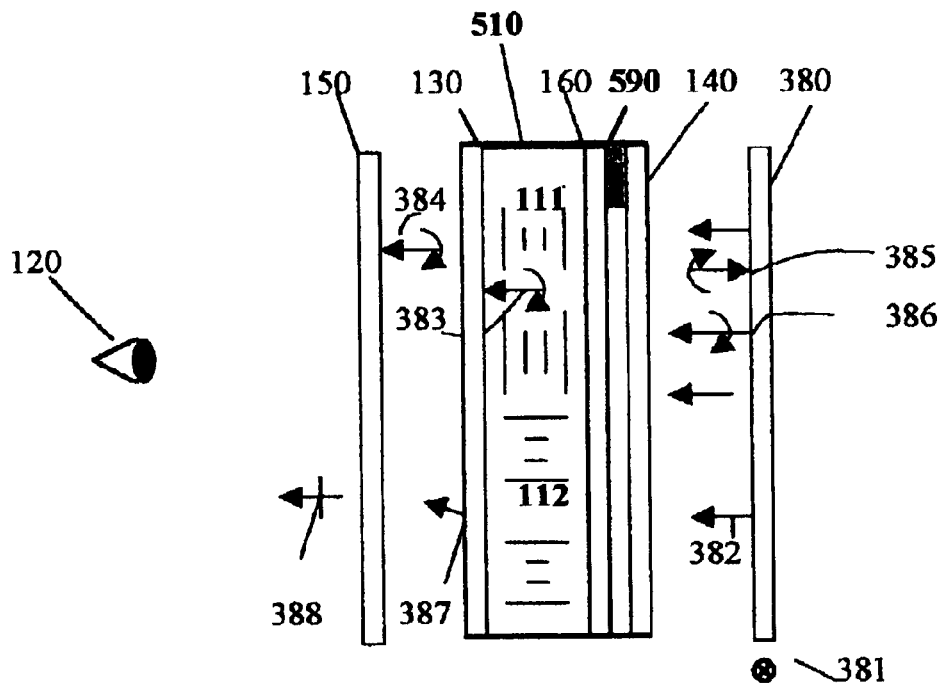

FIG. 5B shows a sectional drawing of non-symmetrical display structure. In order to gain brightness, the front-lit display mode is a black-and-white mode because the color filter (CF) 590 layer is positioned at the back of the REP layer 260. The polarity of ChLC material 111 can be either the same as or different from the AEP 150. In the front-lit mode, front AEP 150 has the same polarity as the REP 160 but opposite to the cholesteric liquid crystals inside the display cell 110. The Bragg reflection out of 110 will be substantially cut off by the front AEP 150, so that the color information is merely generated by the REP 160 and the color filter 590. The paper white optical ON state takes on in the planar texture area, and the black optical OFF state in the focal conic texture area respectively. In the back-lit mode, the front AEP 150 has the opposite polarity to the reflective polarizer. Back light emitting from light panel 380 passing REP 160 becomes left polarized light without substantially attenuation. The light, which passing through the color filter 590 and through the ChLC layer 111, will be blocked by 150. On the other hand, the color light that travels through the focal conic texture 112 will be depolarized and finally emerges to the front viewer.

Figure 6:
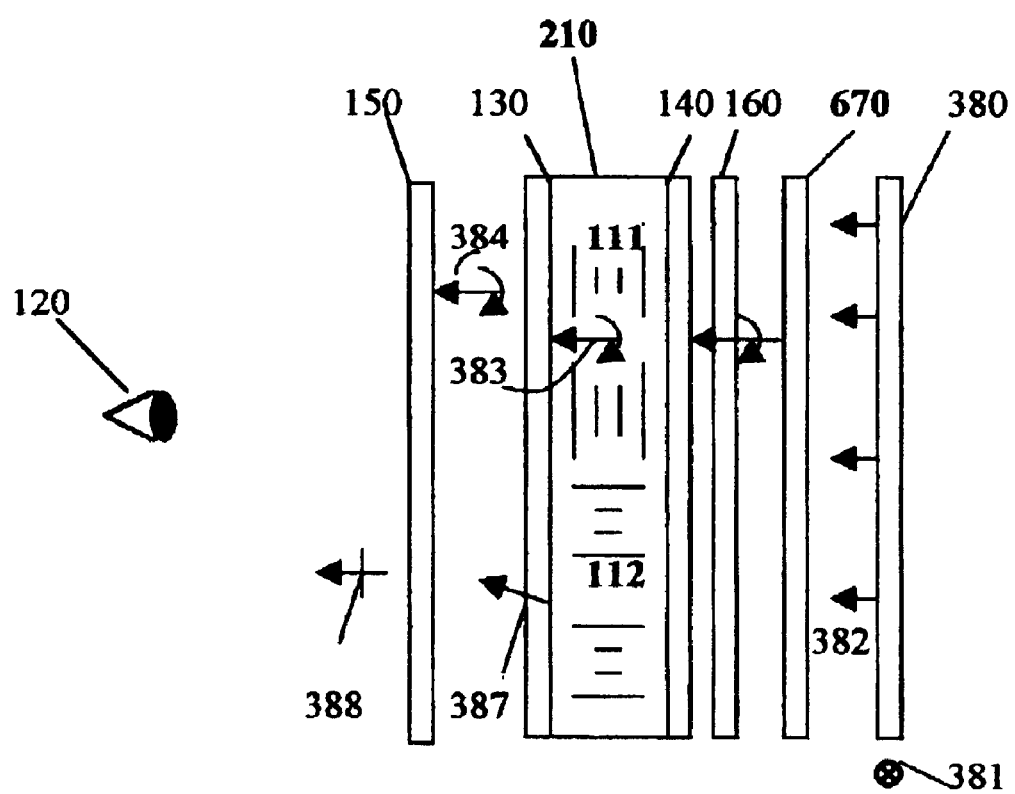
FIG. 6 shows a schematic display structure with a contrast ratio enhancement component.

Turning now to FIG. 6, illustrated is a sectional drawing of a back-lit display mode. A contrast ratio enhancement layer 670 is positioned between the back lighting panel 380 and reflective elliptical polarizer 160. The function of the layer 670 is converting the back light into the elliptical polarization. In such a structure, the display's darkness in the planar texture area not only depends on the 150 and 160, but also on the enhancement layer 670. 670 may be an absorptive polarizer or a combination of the absorptive polarizer and reflective polarizer. Again, the latter has the light recycling characteristics. Note, the function of the layer 670 is only for the purpose of contrast ratio enhancement, not for the brightness enhancement as described in the prior arts.

Figure 7A:
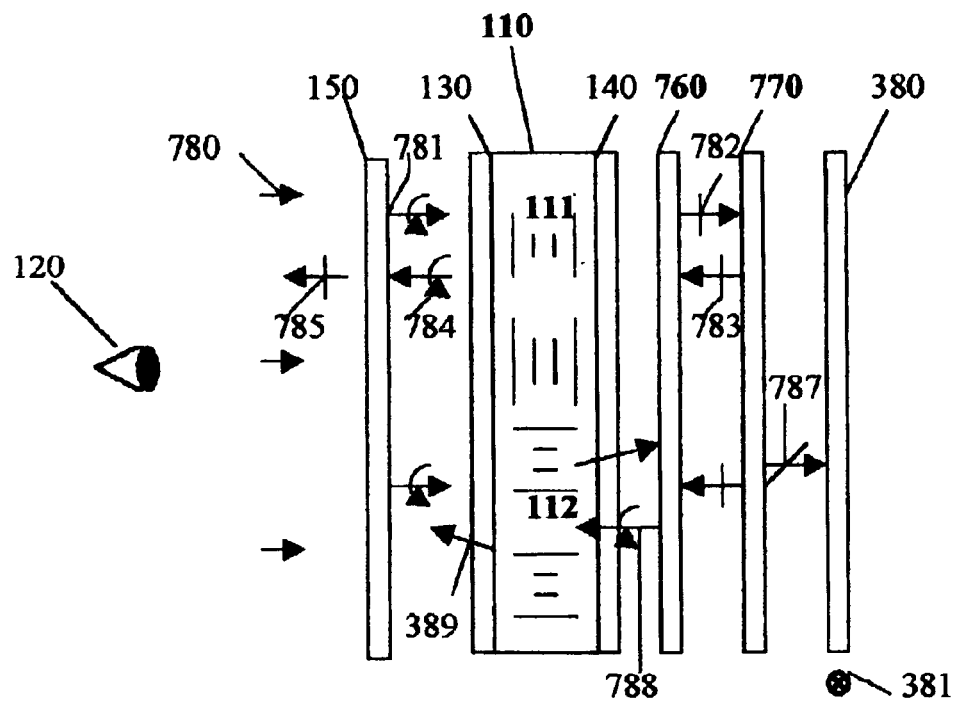
FIG. 7 shows a schematic dual-mode display structure employing a linear reflective polarizer where 7A represents a front-lit mode and 7B represents a back-lit mode.

Turning now to FIG. 7, illustrated is a sectional drawing of a display structure employing a reflective linear polarizer (RLP). It is basically the same as the FIG. 1 except the back reflective polarizer instead of a cholesteric polarizer. The reflective polarizer here in the FIG. 7 is composed of a reflective linear polarizer 770 and a retardation film (RF) 760 laminated with each other. A BEF (brightness enhancement film) film and DBEF (double brightness enhancement film) film from 3M can be utilized as the reflective linear polarizer, but there is no need of any aluminum or other metal reflector like the prior art does.

The principle of DBEF in the dual-working cholesteric display mode can be described as follows: The DBEF has a basic function of linear polarization reflection and transmission. For example, horizontal component is being reflected, and vertical polarization is transmitted. In a specific application of a reflective display, a quarter-wave retarder is necessary to convert the linear reflective polarization into circular polarization. If an optional retarder film other than quarter-wave is used, an elliptical reflective polarizer will be obtained. The function of such composite film is equivalent to the cholesteric elliptical polarizer described in the FIG. 1. The light passing through the front AEP 150 becomes right-handed elliptical polarization 781, and then it passes through the ChLC cell structure in the planar state, and remains its phase and intensity. Finally, such elliptical polarization is reflected by the reflective RF/DBEF circular polarizer 760/770. On the other hand, when the above-mentioned elliptical polarization passes through the ChLC cell structure in the focal conic state, it will become depolarized and scattered. The scattered light proceeds to hit on the reflective elliptical polarizer, only the light 788 with the same polarity as the RF/DBEF structure has a chance to reflect back to the CHLC cell structure and once again being depolarized. The component with the opposite polarity will pass through RF/DBEF composite films and absorbed by either black coating or by the black housing structure between 770 and 380. Finally, only a small percentage of the incoming light has the chance to penetrate through the front polarizer after the multi-pass absorption.

Figure 7B:
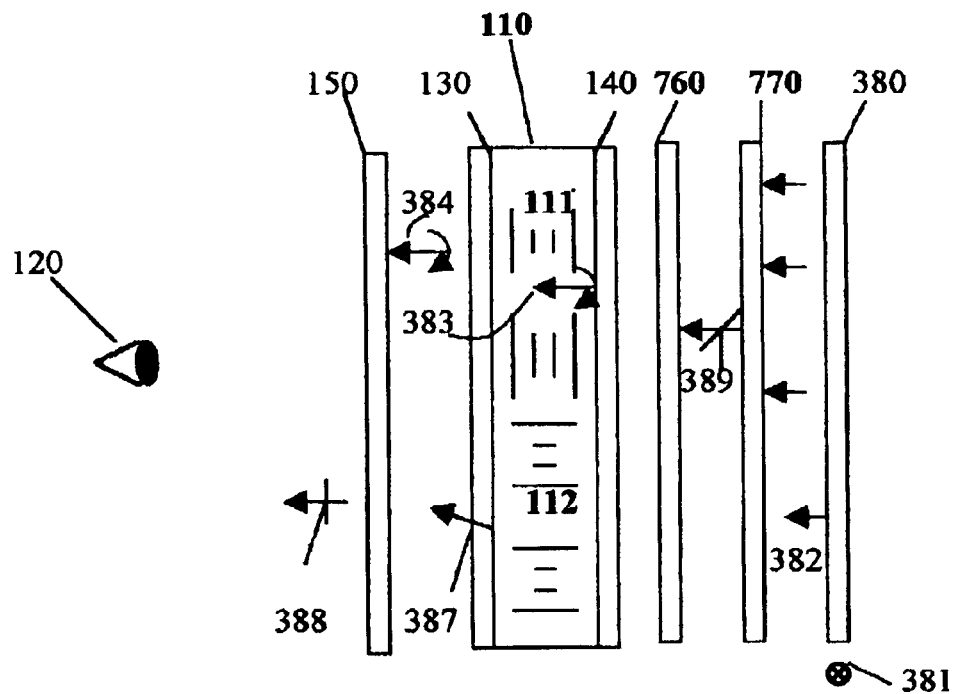

FIG. 7B shows a back-lit mode of the ChLC display employing a RF/DBEF/RF composite structure. In order to create light recycle properties to the back-lit panel, the second retardation film is positioned between the back-light panel and the DBEF film. The working principle is described as follows. A light beam 382 generated from the back-lit panel 380 reaches the composite structure 760/770, half of it transmits through the composition and half of it reflects back to the back-lit panel and bounces back from the back-lit panel while its polarity changes. As a result, both the first half transmission and the second half recycling component, through the composite structure 383, becomes elliptical polarization with the opposite polarity to the front absorptive polarizer150. When the light 383 passes through the ChLC cell structure in the planar texture area, it will remain substantially its polarity and intensity, which finally is blocked (absorbed) by the front REP 150, so that the display takes on an optical OFF state or dark state. When the light 383 passes through the ChLC cell structure in the focal conic texture area, it will be substantially depolarized and scattered 387, and 50% of the light will pass through the polarizer film and emerge to the front of the display. Thus the display takes on an optical ON or bright white state.

In principle, any of the reflective linear polarizer film could be utilized within the scope of the present invention with the condition of the combination of a required retardation film.

I claim:

1. A reflective paper white display comprising:
   a. an absorptive elliptical polarizer, and
   b. a reflective elliptical polarizer with a polarity the same as the absorptive elliptical polarizer, and
   c. a darkening layer, and
   d. a plurality of transparent conductive patterned substrates juxtaposed to form a cell structure, and
   e. a cholesterics material with predetermined polarity and with at least one controllable optical ON texture and at least one controllable OFF texture respectively, and
   f. the cell structure enclosing the cholesteric material within inside surfaces, attaching the absorptive elliptical polarizer on the front outside surface and the reflective elliptical polarizer on the back outside surface, and combining the darkening layer at the utmost back side of the structure, whereby a paper white ON state will be displayed in the controllable optical ON texture area of the cholesterics;

whereby a black OFF state will be displayed in the controllable optical OFF texture area of the cholesterics.

2. The reflective display as in claim 1 wherein the paper white ON state is generated by the reflective elliptical polarizer reflecting a broadband spectrum of incoming light in the controllable planar texture area and in the controllable field-induced nematic texture area.

3. The reflective display as in claim 1 wherein the black optical OFF state is generated by a multi-pass absorption in the controllable focal conic texture area.

4. The reflective display as in claim 1 wherein the absorptive elliptical polarizer is a composite structure of an optional retardation film laminated with an absorptive linear polarizer at an optional angle.

5. The reflective display as in claim 1 wherein the reflective elliptical polarizer is a wide band reflective cholesteric polymeric film.

6. The reflective display as in claim 1 wherein the reflective elliptical polarizer is a composite structure of a reflective linear polarizer and an optional retardation film.

7. The reflective display as in claim 1 wherein the reflective elliptical polarizer is positioned inside of the back substrate of the display cell structure.

8. The reflective display as in claim 1 further including a color filter layer positioned inside of the back substrate and in front of the reflective elliptical polarizer to achieve a reflective full color display.

* * * * *